United States Patent [19]

Richter, Jr.

[11] 4,078,289

[45] Mar. 14, 1978

[54] METHOD FOR FORMING A LONG-LIFE THERMAL CRACK RESISTANT TRAP

[75] Inventor: Albert P. Richter, Jr., Houston, Tex.

[73] Assignee: Texaco Inc., New York, N.Y.

[21] Appl. No.: 751,493

[22] Filed: Dec. 17, 1976

Related U.S. Application Data

[60] Continuation-in-part of Ser. No. 455,770, Mar. 28, 1974, abandoned, which is a division of Ser. No. 315,949, Dec. 18, 1972, Pat. No. 3,834,125.

[51] Int. Cl.² .................. B23P 13/00; B23P 15/00
[52] U.S. Cl. ........................ 29/157 R; 29/DIG. 26
[58] Field of Search ........ 29/157 R, 157 A, DIG. 26; 408/1 R; 138/115, 111, DIG. 11; 165/164, 178, 61; 55/33, 62, 74, 75, 179, 208, 316, 381, 389

[56] References Cited

U.S. PATENT DOCUMENTS

| 2,210,744 | 8/1940 | Winder | 138/115 |
|---|---|---|---|
| 2,309,666 | 2/1943 | Parker | 29/157 R |
| 2,324,707 | 7/1943 | Johnson | 165/164 |
| 2,755,506 | 7/1956 | Weber | 165/61 |
| 2,778,609 | 1/1957 | Peeps | 138/137 |
| 3,243,873 | 4/1966 | Steel | 29/157 A |
| 3,264,803 | 8/1966 | Read | 55/208 |
| 3,476,869 | 11/1969 | Hawkins | 138/111 |
| 3,626,671 | 12/1971 | Ebeling, Jr. | 55/179 |
| 3,734,293 | 5/1973 | Biskis | 55/208 |
| 3,886,638 | 6/1975 | Hayman et al. | 29/DIG. 26 |

FOREIGN PATENT DOCUMENTS

| 532,274 | 9/1930 | Germany | 29/157 R |
|---|---|---|---|
| 1,954,733 | 5/1971 | Germany | 138/111 |
| 98,342 | 3/1940 | Sweden | 138/111 |

*Primary Examiner*—C.W. Lanham
*Assistant Examiner*—Daniel C. Crane
*Attorney, Agent, or Firm*—Carl G. Ries; Thomas H. Whaley; Theron H. Nichols

[57] ABSTRACT

A method for forming a long-life gas trap comprises basically (a) machining an elongated solid element in a cruciform cross-sectional shape from mill stock for forming a housing with four arms, (b) machining each arm to a square cross-section with four flat surfaces thereon, (c) boring a hole centrally and longitudinally of the housing for forming an elongated chamber having a longitudinal axis, (d) boring a hole parallel to the elongated chamber in each of the four arms of the cruciform shaped housing contiguous to the elongated chamber for forming four tubes contiguous with the four sides of the elongated chamber, and (e) bending the ends of at least four of the tubes with a bending fixture having a roller to a position normal to the longitudinal axis for forming a gas trap that has longer life because of the high resistance to cracking due to continuously alternating between thermal expansion and contraction.

9 Claims, 5 Drawing Figures

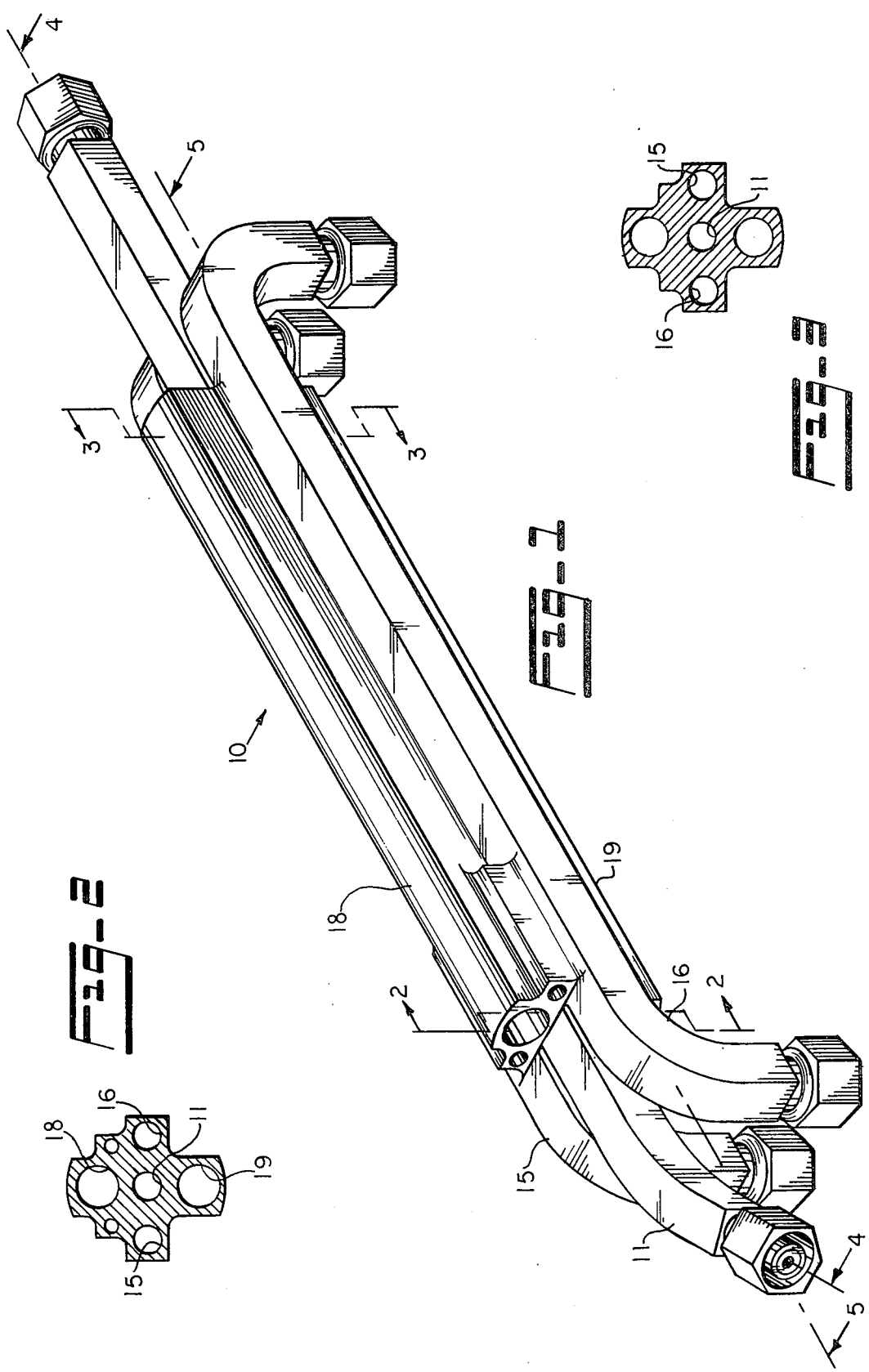

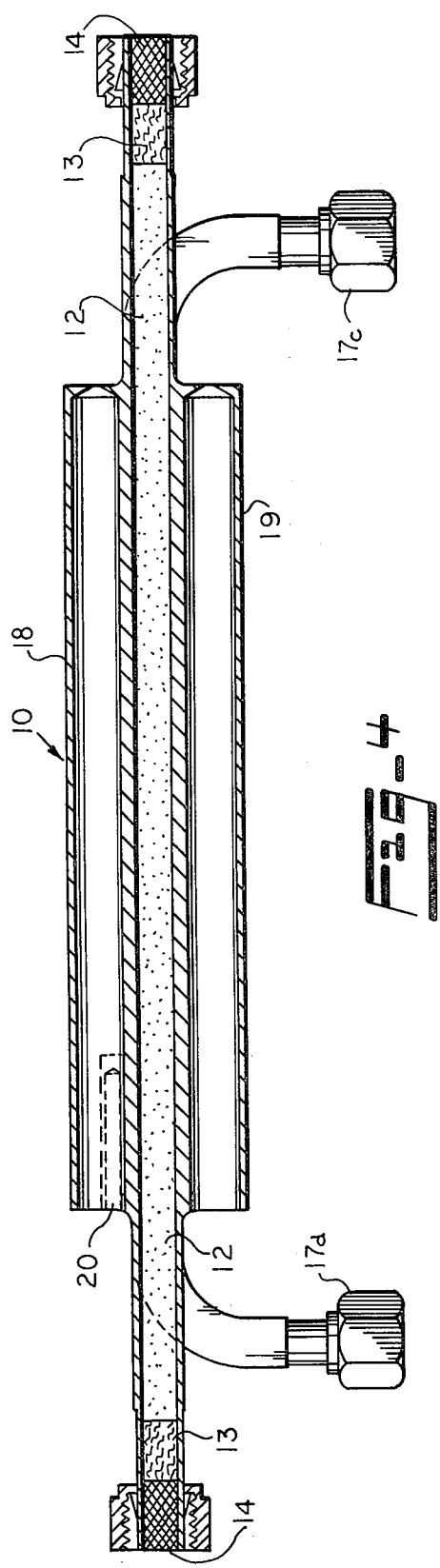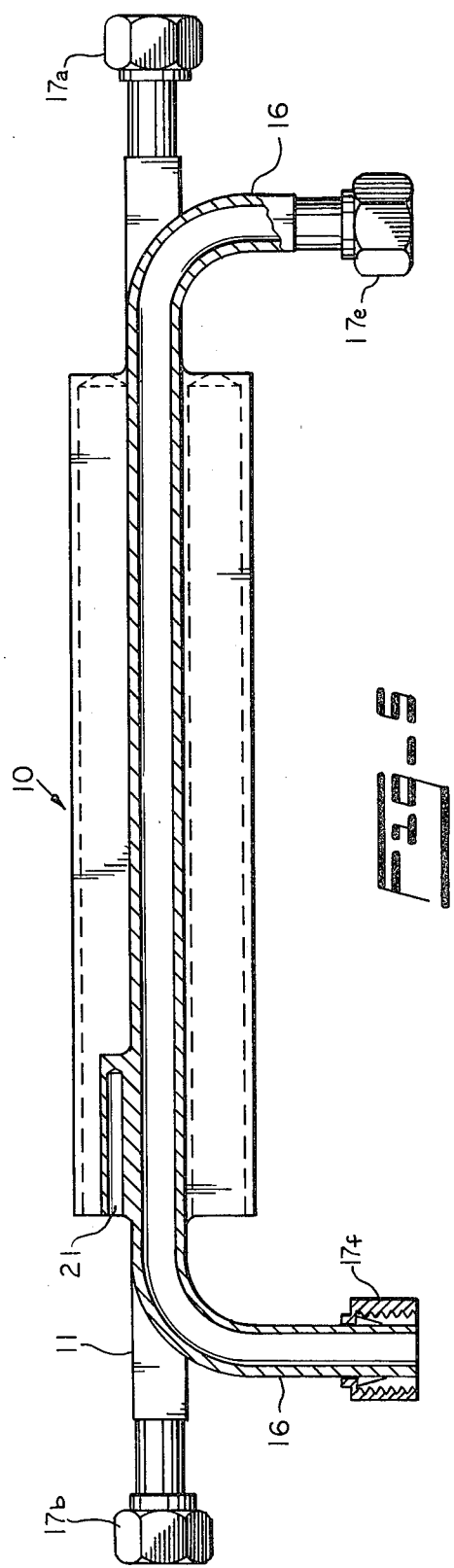

METHOD FOR FORMING A LONG-LIFE THERMAL CRACK RESISTANT TRAP

BACKGROUND OF THE INVENTION

This is a Continuation-in-Part of application Ser. No. 455,770, filed Mar. 28, 1974, now abandoned, which was a division of application Ser. No. 315,949, filed Dec. 18, 1972, now U.S. Pat. No. 3,834,125, issued Sept. 10, 1974.

Manufacturing a gas trap that will withstand rapid alternation between very low temperatures and very high temperatures is difficult to accomplish with any degree of economy in materials and labor, and yet maintain a substantial amount of reliability.

One method provides a means of analyzing a gas stream, as for hydrocarbon content, which extracts the hydrocarbons by using a molecular sieve, an examplar filter material being "Carbosieve", a carbon molecular sieve material. These materials absorb hydrocarbons at low temperature and release them at elevated temperature. If a continuous gas stream is to be examined for hydrocarbon content, it is necessary to sample the gas for a period of time with the filter material at a low temperature, stop the sample gas flow and extract the collected hydrocarbons by bringing the filter material to an elevated temperature and flushing with a flush gas. It is often desirable to sample and extract at a rapid rate, particularly when the hydrocarbon level is changing. This can be conveniently accomplished by means of a device, called a trap, that contains the filter material and suitable means for heating and cooling the filter material. Such a device is difficult to design and build that has high resistance to thermal cracking and accordingly has a long life.

OBJECTS OF THE INVENTION

Accordingly, a primary object of this invention is to provide a method for forming a reliable and long life trap that can be alternately and rapidly heated and cooled as well as contain a filter material.

Another primary object of this invention is to provide a method for forming a gas trap with a filter material that has a high heat transfer area to the filter material and a low thermal mass.

A further object of this invention is to provide a method for forming a highly efficient gas trap that will withstand rapid temperature changes and have very little difference in expansion rates of the different parts of the gas trap.

Another object of this invention is to provide a method for forming a gas trap that will not crack due to differences in thermal coefficients of expansion between the different materials and parts of the gas trap.

Still another object of this invention is to provide a method for forming a gas trap having a straight tube for containing the filter material for permitting straight forward packing of the trap.

A still further object of this invention is to provide a method for forming a highly efficient gas trap that will not crack due to rapid variations in thermal expansion and which is easy to operate, is of simple configuration, is economical to build and assemble, and is of greater efficiency while it is alternately and rapidly heated and cooled as well as alternately rapidly heating and cooling the filter material therein.

BRIEF DESCRIPTION OF THE DRAWINGS

The drawings diagrammatically illustrate by way of example, not by way of limitation, one form or mechanism made by the new method of the invention wherein like reference numerals have been employed to indicate similar parts in the several views in which:

FIG. 1 is a schematic perspective view of a gas trap made by the method of the invention;
FIG. 2 is a section taken at 2—2 on FIG. 1;
FIG. 3 is a section taken at 3—3 on FIG. 1;
FIG. 4 is a section taken at 4—4 on FIG. 1; and
FIG. 5 is a section taken at 5—5 on FIG. 1;

DESCRIPTION OF THE INVENTION

The invention disclosed herein, the scope of which being defined in the appended claims, it not limited in its application to the details of the methods for forming the construction and arrangements of parts shown and described, since the invention is capable of other methods for forming other embodiments and of being practiced or carried out in various other ways. Also, it is to be understood that the phraseology or terminology employed herein is for the purpose of description and not of limitation. Further, many modifications and variations of the invention as hereinbefore set forth will occur to those skilled in the art. Therefore, all such modifications and variations which are within the spirit and scope of the invention herein are included and only such limitations should be imposed as are indicated in the appended claims.

A basic method for forming a long-life gas trap as illustrated in FIG. 1 comprises the following steps:

1. machining an elongated solid element in a cruciform cross-sectional shape for forming a housing with four arms,
2. machining each arm to a square cross-section,
3. boring a hole centrally and longitudinally of the housing for forming an elongated chamber having a longitudinal axis,
4. boring a hole parallel to the elongated chamber in each of the four arms of the cruciform shaped housing contiguous to the elongated chamber for forming four tubes contiguous with the four sides of the elongated chamber,
5. making two cuts on two opposite arms at each end of the cruciform elongated element for forming three square tubes protruding from each end, and
6. bending the ends of at least four of the square tubes to a position normal to the longitudinal axis.

More details of step (1) of the above basic method comprises:

1. machining the elongated solid element in a cruciform cross-sectional shape from mill stock for forming the housing with four arms.

Further details of the last step of the above basic method comprises:

1. bending each arm 90° with a coventional bending fixture or arm having a roller on the end thereof for bending as by rolling the square tube over a metal form having the desired radius of curvature whereby strength of the cross-section retains the bore shape during bending without requiring the insertion of a mandrel.

More details of step (6) of the above basic method comprises:

1. bending the ends of at least two of the square tubes on each end of the cruciform elongated element to a position normal to the longitudinal axis.

Another method may include the steps of the above basic method plus the following step of:

1. machining each of the ends of the four arms for pipe connections.

Another method comprises modifying the fifth step as follows:

1. machining as by sawing two opposite arms on each end of the elongated cruciform element for forming at least two square tubes protruding from each end of the element.

Another method comprises modifying the fifth step as follows:

1. machining as by sawing two opposite arms on each end of the elongated cruciform element for forming three square tubes protruding from each end of the element.

While various long-life gas traps may be formed or manufactured by the above methods, a preferred gas trap is disclosed hereinafter.

FIG. 1, a schematic perspective view of the preferred gas trap made by the method of the invention, discloses how each part of the new gas trap 10 is formed by the above described methods into one homogeneous integral mechanism.

The new gas trap 10, FIG. 1, comprises the heaters and coolers formed integral with the elongated chamber holding the filter material and through which all of the gas mixture must flow.

A substantially straight elongated chamber 11, FIG. 1, is bored and formed in the center of the gas trap, particularly as illustrated in the sectional views of FIGS. 2 and 3 taken near the respective fore and aft ends of the gas trap.

As illustrated in FIG. 4, a section at 4—4 on FIG. 1, a molecular sieve, as a carbon molecular sieve 12 is substantially centered in the chamber 11 with a packing comprising a glass wool packing 13 at each end held in position by a fine mesh copper screen 14 extending to the ends of the chamber. Carbon molecular sieve 12 is a conventional molecular sieve, such as one using the filter material "Carbosieve", having regular channels of molecular dimensions throughout which are large enough to admit various small molecules of gas or water but not large enough to admit hydrocarbon molecules. Suitable pipe connections 17a, 17b, FIG. 5, are provided for connecting the elongated chamber 11 to the source of the gas mixture (not shown) for receiving thereof and for connecting to a gas analyzer (not shown) for analyzing the gas separated from the mixture.

Preferably, gas trap 10 is machined in one piece and then both tube ends of elements 15 and 16 are bent to the desired shape as described in detail hereinbefore.

Coolers 15 and 16, FIGS. 1 - 3, are mounted in integral relationship with the two sides of the chamber 11 for maximum area of contact with a full one-half of the outer surface of the chamber. A refrigerant as an alcohol is circulated through each of the coolers 15 and 16 for cooling of the elongated chamber and particularly for cooling the molecular sieve therein. Suitable and similar pipe connections 17c, 17d, and 17e, 17f are provided on the respective coolers 15 and 16, FIGS. 4 and 5.

Heaters 18 and 19, FIGS. 1 and 2, are formed likewise in integral relationship with the other two sides, the top and the bottom of the elongated chamber 11, as illustrated, for maximum area of contact with the other half of the outer surface of the chamber. An electric heating element (not shown) is positioned in each of the bored cavities in heaters 18 and 19. Thermocouples 20 and 21, FIGS. 4 and 5, respectively, are mounted integrally in heater 19 for monitoring and controlling the maximum temperatures of the gas trap.

Briefly, in operation of the disclosed gas trap 10, FIG. 1, for extracting a gas, as hydrocarbons in the preferred instance for further analyzing, a sample of the gas mixture is passed through chamber 11 and through the carbon molecular sieve therein for a predetermined period of time. During this period, the filter material 12, FIG. 4, therein chamber 11 is maintained cooled at a predetermined low temperature by the coolers integral with both sides of the chamber. At the end of this time period, the gas flow is stopped and the collected hydrocarbons are extracted by rapidly bringing the filter material 12, FIG. 4, to the predetermined elevated temperature and flushing the chamber 11 with a flush gas, as helium. For a continuous gas stream, this operation is repeated continuously. Likewise, it is often desirable to sample and extract gas at a rapid rate, particularly when the hydrocarbon level is changing. This rapid sampling with the attendant and rapid cooling and heating of the whole gas sampler is easily, conveniently, and reliably accomplished with the disclosed gas trap, the disclosed gas trap having a long life compared to prior gas samplers due to its ability to accept high thermal stresses due to the rapid changes in temperature.

Thus accordingly, it will be seen that the present methods for forming highly efficient, long life gas trap operates in a manner which meets each of the objects set forth hereinbefore.

While only a few methods for forming one embodiment of the invention have been disclosed, it will be evident that various other methods for forming various other modifications are possible in the arrangement and construction of the disclosed long life gas trap without departing from the scope of the invention, and it is accordingly desired to comprehend within the purview of this invention such methods and modifications as may be considered to fall within the scope of the amended claims.

I claim:

1. A method for forming a long-life gas trap comprising the steps of,
   a. machining an elongated solid element in a cruciform cross-sectional shape for forming a housing with four arms,
   b. machining each arm to a substantially square cross-section,
   c. boring a hole longitudinally of the housing for forming an elongated chamber having a longitudinal axis,
   d. boring a hole parallel to the elongated chamber in each of the four arms of the cruciform shaped housing contiguous to the elongated chamber for forming four tubes contiguous with the four sides of the elongated chamber,
   e. machining two opposite arms on each end of the elongated cruciform element for forming at least two square tubes protruding from the elongated cruciform elements, and
   f. bending the ends of at least two of the square tubes to a position normal to the longitudinal axis for increased resistance to cracking due to continuously alternating between thermal expansion and contraction.

2. A method as recited in claim 1 including the additional step of,
   g. machining each of the ends of the four arms for pipe connections.

3. A method as recited in claim 1 wherein the bending step (f) comprises further,
   h. bending each arm 90° with a bending fixture arm having a roller thereon for bending as by rolling each square tube over a form having the desired radius of curvature whereby strength of the cross-section retains the bore shape during bending without requiring the insertion of a mandrel.

4. A method as recited in claim 1 wherein the first step (a) comprises,
   machining an elongated solid element from mill stock in a cruciform cross-sectional shape for forming a long-life gas trap housing with four arms.

5. A method as recited in claim 1 wherein the fifth step (e) comprises,
   machining two opposite arms on each end of the elongated cruciform element for forming at least three square tubes protruding from each end of the element.

6. A method as recited in claim 1 wherein the fifth step (e) comprises,
   machining two opposite arms on each end of the elongated cruciform element for forming three square tubes protruding from each end of the element.

7. A method as recited in claim 5 wherein the step (e) comprises further,
   sawing the two opposite arms on each of the elongated cruciform element for forming at least two square tubes protruding from each end of the element.

8. A method as recited in claim 6 wherein the step (e) comprises further,
   sawing the two opposite arms on each end of the elongated cruciform element for forming three square tubes protruding from each end of the element.

9. A method for forming a thermal crack resistant gas trap comprising the steps of,
   a. machining an elongated solid element from mill stock in a cruciform cross-sectional shape for forming a housing with four arms,
   b. machining each arm to a square cross-section,
   c. boring a hole longitudinally of the housing for forming an elongated chamber having a longituinal axis,
   d. boring a hole parallel to the elongated chamber in each of the four arms of the cruciform shaped housing contiguous to the elongated chamber for forming four tubes contiguous with the four sides of the elongated chamber,
   e. sawing two opposite arms on each end of the elongated cruciform element for forming at least four square tubes protruding from the elongated cruciform elements, and
   f. bending each arm 90° over a roller on a bending fixture whereby strength of the cross-section retains the bore shape during bending without requiring the insertion of a mandrel.

* * * * *